(12) United States Patent
Mukkamala et al.

(10) Patent No.: US 6,602,832 B2
(45) Date of Patent: Aug. 5, 2003

(54) OIL-SOLUBLE ADDITIVE COMPOSITIONS FOR LUBRICATING OILS

(75) Inventors: Ravindranath Mukkamala, Houston, TX (US); Rajiv Manohar Banavali, Huntingdon Valley, PA (US)

(73) Assignee: Crompton Corporation, Middlebury, CT (US)

( * ) Notice: Subject to any disclaimer, the term of this patent is extended or adjusted under 35 U.S.C. 154(b) by 0 days.

(21) Appl. No.: 10/054,064

(22) Filed: Jan. 22, 2002

(65) Prior Publication Data

US 2002/0137638 A1 Sep. 26, 2002

Related U.S. Application Data

(60) Provisional application No. 60/263,775, filed on Jan. 24, 2001.

(51) Int. Cl.$^7$ .............................................. C10M 14/06
(52) U.S. Cl. ........................ 508/284; 508/459; 508/525
(58) Field of Search ................................ 508/284, 459, 508/525

(56) References Cited

U.S. PATENT DOCUMENTS

| | | | | |
|---|---|---|---|---|
| 2,767,143 A | * | 10/1956 | Caffrey et al. | 508/284 |
| 2,868,727 A | * | 1/1959 | Hughes | 507/243 |
| 3,108,071 A | * | 10/1963 | Harker | 508/284 |
| 4,189,587 A | * | 2/1980 | Holt et al. | 548/301.4 |
| 5,188,745 A | * | 2/1993 | Migdal et al. | 508/255 |
| 5,935,913 A | * | 8/1999 | Nalesnik et al. | 508/255 |
| 6,013,200 A | * | 1/2000 | Prince | 252/391 |
| 6,187,722 B1 | * | 2/2001 | Rowland et al. | 508/284 |

\* cited by examiner

*Primary Examiner*—Jacqueline V. Howard
(74) *Attorney, Agent, or Firm*—Daniel Reitenbach

(57) ABSTRACT

An oil-soluble lubricant additive composition comprising:

(a) at least one compound of formula I:

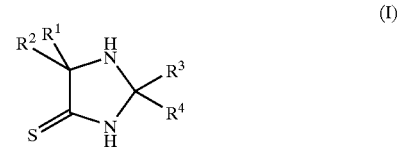

wherein $R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring; and (b) an acid having the formula $RCO_2H$, wherein R is $C_1$–$C_{25}$ alkyl, $C_2$–$C_{25}$ alkenyl, $C_2$–$C_{25}$ alkynyl, $C_5$–$C_{25}$ aryl or $C_5$–$C_{25}$ aralkyl.

10 Claims, No Drawings

OIL-SOLUBLE ADDITIVE COMPOSITIONS FOR LUBRICATING OILS

CROSS REFERENCE TO RELATED PATENT APPLICATIONS

This is a non-provisional application of prior pending U.S. provisional application serial No. 60/263,775 filed Jan. 24, 2001.

BACKGROUND

This invention relates generally to compositions useful as ashless oil-soluble additives for lubricating oils.

Zinc dialkyldithiophosphates (ZDDP) are widely used as lubricant additives. The principal disadvantages of these compounds are that an ash residue is produced by the zinc as the additive is consumed, and that phosphorus is known to affect the efficiency of catalytic converters in motor vehicles, thereby causing emissions problems. An ashless, non-phosphorus alternative to ZDDP would be extremely useful.

A limited number of alkyl-substituted imidazolidinethione compounds is disclosed in A. E. Oberster et al. in Rubber Chem. Technol., vol. 41, page 255 (1968), but there is no suggestion therein that such compounds would be effective as a component in additive compositions for lubricating oils.

The problem addressed by this invention is to find improved phosphorus-free ashless oil-soluble additives for lubricating oils.

STATEMENT OF INVENTION

The present invention is directed to an oil-soluble lubricant additive composition comprising:

(a) at least one compound of formula I:

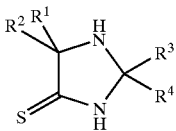

(I)

wherein $R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring; and (b) an acid having the formula $RCO_2H$, wherein R is $C_1$–$C_{25}$ alkyl, $C_2$–$C_{25}$ alkenyl, $C_2$–$C_{25}$ alkynyl, $C_5$–$C_{25}$ aryl or $C_5$–$C_{25}$ aralkyl.

The present invention is further directed to a lubricating oil composition comprising a lubricating oil and from 0.1% to 20% by weight of the lubricant additive composition described above.

DETAILED DESCRIPTION

An "alkyl" group is a hydrocarbyl group having, unless otherwise specified, from one to twenty-five carbon atoms in a linear, branched or cyclic arrangement. Substitution on alkyl groups of one or more halo, hydroxy, alkoxy, alkanoyl or amido groups is permitted; alkoxy, alkanoyl and amido groups may in turn be substituted by one or more halo substituents. An "alkenyl" group is an "alkyl" group having at least two carbon atoms in which at least one single bond has been replaced with a double bond. An "alkynyl" group is an "alkyl" group having at least two carbon atoms in which at least one single bond has been replaced with a triple bond. An "aryl" group is a substituent derived from an aromatic compound, including heterocyclic aromatic compounds having heteroatoms chosen from among nitrogen, oxygen and sulfur. An aryl group has a total of from five to twenty-five ring atoms, unless specified otherwise, and has one or more rings which are separate or fused. Substitution on aryl groups of one or more halo, alkyl, alkenyl, hydroxy, alkoxy, alkanoyl or amido groups is permitted, with substitution by one or more halo groups being possible on alkyl, alkenyl, alkoxy, alkanoyl or amido groups. An "aralkyl" group is an "alkyl" group substituted by an "aryl" group.

The additive composition of the present invention includes at least one compound of formula (I). It is preferred that none of $R^1$, $R^2$, $R^3$ or $R^4$ is hydrogen, i.e., four alkyl, alkenyl, aryl or aralkyl groups are present; in the case where the groups are alkyl, the compound of formula (I) is a tetraalkylimidazolidinethione (TAIT). The compound in which $R^1$, $R^2$, $R^3$ and $R^4$ are all methyl, i.e., tetramethylimidazolidinethione is also known as TMIT, and has the following structure:

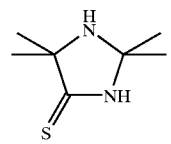

In one aspect of this invention, the additive composition contains a mixture of TAIT compounds produced from a mixture of ketones. In another aspect of this invention, the composition contains a mixture of tetrasubstituted compounds and compounds having less than four alkyl groups, i.e., those in which one or more of the substituents is hydrogen; such a mixture would be produced from a mixture of ketones and aldehydes, or from a mixture of aldehydes.

It is preferred that the group R in the acid, $RCO_2H$, has from five to 17 carbon atoms. When R is alkyl or alkenyl, it is further preferred that R has from nine to 17 carbon atoms.

In the lubricant additive composition, the molar ratio of the compound of formula (I) to the acid $RCO_2H$ is preferably in the range from 3:1 to 1:5, and most preferably, from 2:1 to 1:2. For the purpose of calculating molar ratios in a case where multiple compounds of formula (I) are present, an approximate molecular weight is determined for the mixture using NMR spectral analysis of the product mixture, and averaging the molecular weights of the two predominant products.

In one aspect of this invention, the lubricant additive composition is added to a lubricating oil in an amount from 0.1% to 20% by weight. It is preferred that the additive composition is added in an amount from 0.1% to 10%, more preferably from 0.5% to 10%, and most preferably from 0.5% to 3%. A lubricating oil is a natural or synthetic oil, having suitable viscosity for use as a lubricant, or a mixture thereof.

EXAMPLES

Tetramethylimidazolidinethione (TMIT)

This compound was prepared according to the procedure given in U.S. Pat. No. 5,057,612, as follows.

To a mechanically-stirred mixture of ammonium sulfide (0.4 moles, 136 mL, 20 wt % aqueous solution), sodium cyanide (14.7 g, 0.3 moles), ammonium chloride (16.1 g, 0.3 moles) and water (80 mL), acetone (44 mL, 0.6 moles) was added drop-wise over a period of 30 min.; during the addition of acetone, the reaction temperature rose to about 36° C. The reaction mixture was then externally heated to 65° C. for a period of 6–7 hours. The reaction mixture was cooled to 0–5° C. using an ice bath, and the product (obtained as a white solid) was filtered, washed with cold water and suction-dried. The yield of TMIT was 44.6 grams (94%); melting point: 155° C. IR: 3521, 2976, 1657, 1524, 1462 cm$^{-1}$; $^1$H NMR (CDCl$_3$, 500 MHz): δ1.46 (s, 6 H), 1.44 (s, 6 H) ppm; $^{13}$C NMR (CDCl$_3$, 125 MHz): δ207.7, 78.4, 70.9, 29.9, 29.9 ppm.

7,14-diazadispiro[5.1.5.2]pentadecane-15-thione (DDPT)

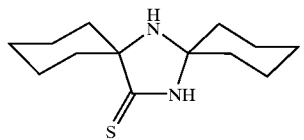

The procedure described for preparation of TMIT was used, starting with a mixture of ammonium sulfide (0.4 moles, 136 mL, 20 wt % aqueous solution), sodium cyanide (14.7 g, 0.3 moles), ammonium chloride (16.1 g, 0.3 moles) and water (80 mL); with addition of cyclohexanone (58.8 g, 0.6 moles). The product was obtained as a white solid (69.8 grams, 98%), and melted at 229° C. IR: 3127, 2925, 2855, 1516, 1454 cm$^{-1}$; $^1$H NMR (CDCl$_3$, 500 MHz): δ9.8 (bs, 1H), 1.9(dt, 2H), 1.8-1.2 (m, 18H) ppm; $^{13}$C NMR (CDCl$_3$, 125 MHz): δ207.8, 81.0, 72.9, 39.6, 37.8, 24.9, 24.6, 23.0, 21.9 ppm.

Example 1

TMIT Combined with Stearic Acid

TMIT and stearic acid were mixed at a 1:1 mole ratio and heated in a sand bath at about 140° C. for one hour and cooled to room temperature.

Example 2

DDPT Combined with Stearic Acid

DDPT and stearic acid were mixed at a 1:1 mole ratio and heated in a sand bath at about 140° C. for one hour and cooled to room temperature.

Example 3

TMIT Combined with SYLFAT FA-1

TMIT (1.0 g, 6.33 mmol) and SYLFAT FA-1 (naturally occurring mixture of unsaturated C-18 acids, available from Arizona Chemical Co., Jacksonville, Fla., 1.83 g, ca. 6.33 mmol) were added to a sample vial and heated in a sand bath at about 140° C. for one hour and cooled to room temperature ("r.t.") to produce a clear, thick oil.

Example 4

DDPT Combined with SYLFAT FA-1

DDPT and SYLFAT FA-1 were mixed at a 1:1 mole ratio and heated in a sand bath at about 140° C. for one hour and cooled to room temperature.

Example 5

TAIT Mixture Prepared from Acetone/Methyl Isobutyl Ketone/Cyclohexanone Combined with SYLFAT FA-1

A TAIT mixture was prepared from an equimolar mixture of the three title ketones according to the procedure used for preparation of TMIT, using ammonium sulfide (136 mL, 0.4 moles, 20 wt % aqueous solution), sodium cyanide (14.7 g, 0.3 moles), ammonium chloride (16.1 g, 0.3 moles), water (80 mL), cyclohexanone (19.6 g, 0.2 moles), acetone (11.6 g, 0.2 moles) and methyl isobutyl ketone (20.3 g, 0.2 moles) to obtain a oily layer at the end of the heating period. The oil layer was extracted into chloroform (350 mL), washed with water and dried (anhydrous potassium carbonate). Solvent evaporation yielded the product as a thick oil that slowly turned into a sticky gray solid (20 grams, yield: 30% for an average molecular weight of 219). IR: 3533, 3137, 2925, 1599, 1516, 1450, 1379 cm$^{-1}$; $^1$H NMR (CDCl$_3$, 500 MHz): δ2.12 (d), 1.94 (s), 1.8 (m), 1.62-1.20 (m), 1.12-0.98 (broad m), 0.89 (dd), 0.82-0.76 (m), 0.72 (d) ppm; $^{13}$C NMR (CDCl$_3$, 125 MHz): δ 208.6, 207.2, 206.9, 206.8, 206.6, 124.5, 123.7, 80.7, 80.3, 78.4, 77.9, 77.3, 76.9, 76.7, 73.1, 72.4, 70.3, 69.7, 52.1, 51.0, 49.5, 48.3, 39.3, 38.7, 38.2, 37.4, 36.9, 30.2, 29.5, 24.1, 22.4, 22.1, 21.6, 21.4 ppm. The average molecular weight of 219 was calculated by averaging the molecular weights of the acetone/cyclohexanone cross-product (198) and the methyl isobutyl ketone/cyclohexanone cross-product (240), these being the two predominant products among the 4–5 products detected by proton NMR.

The product was mixed with SYLFAT FA-1 at approximately a 1:1 molar ratio, based on the average molecular weight determined above, and heated in a sand bath at about 140° C. for one hour and cooled to room temperature.

Example 6

TAIT Mixture Prepared from Acetone/Methyl Isobutyl Ketone/Methyl Ethyl Ketone/Cyclohexanone Combined with SYLFAT FA-1

A TAIT mixture was prepared from an equimolar mixture of the four title ketones according to the procedure used for preparation of TMIT, using ammonium sulfide (136 mL, 0.4 moles, 20 wt % aqueous solution), sodium cyanide (14.7 g, 0.3 moles), ammonium chloride (16.1 g, 0.3 moles), water (80 mL), cyclohexanone (14.7 g, 0.15 moles), acetone (8.7 g, 0.15 moles) ethyl methyl ketone (10.8 g, 0.15 moles), and methyl isobutyl ketone (15.0 g, 0.15 moles) to obtain an oily layer at the end of the heating period. The oil layer was extracted into chloroform (350 mL), washed with water and dried with anhydrous potassium carbonate. Solvent evaporation yielded the product as a thick oil that slowly turned into a sticky gray solid (36 grams, yield: 55% for an average molecular weight of 219). IR: 3361, 2962, 2874, 1605, 1520, 1459 cm$^{-1}$; $^1$H NMR (CDCl$_3$, 500 MHz): δ 2.24 (d), 2.06 (s), 1.85-1.91 (m), 1.86-1.56 (m), 1.50-1.46 (m), 1.45-1.34 (m), 1.26-1.11 (bm), 1.39 (t), 0.99 (dd), 0.95-0.84 (m) ppm; $^{13}$C NMR (CDCl$_3$, 125 MHz): δ 207.8, 207.62, 207.60, 207.43, 207.40, 207.01, 206.89, 206.68, 206.66, 81.6, 81.18, 81.14, 80.70, 80.65, 78.38, 78.31, 73.95, 73.30, 72.82, 70.79, 70.46, 70.18 and several peaks between 40-10 ppm. The average molecular weight of 219 was calculated by averaging the molecular weights of the acetone/cyclohexanone cross-product (198) and the methyl isobutyl ketone/cyclohexanone cross-product (240), these being the two predominant products among the 8–10 products detected by proton NMR.

The product was mixed with SYLFAT FA-1 at approximately a 1:1 molar ratio, based on the average molecular weight determined above, and heated in a sand bath at about 140° C. for one hour and cooled to room temperature.

Example 7

TMIT Combined with neo-DECANOIC ACID PRIME

TMIT and neo-DECANOIC ACID PRIME (a branched C-10 acid with the COOH group attached to a tertiary carbon, available from Exxon Chemical Co., Houston, Tex.) were mixed in equimolar amounts and heated in a sand bath at about 140° C. for one hour and cooled to room temperature.

Example 8

TAIT Mixture Prepared from Methyl Ethyl Ketone Combined with neo-DECANOIC ACID PRIME A cis-trans mixture was obtained by applying the procedure used for preparation of TMIT to ammonium sulfide (136 mL, 0.4 moles, 20 wt % aqueous solution), sodium cyanide (14.7 g, 0.3 moles), ammonium chloride (16.1 g, 0.3 moles), water (80 mL), and ethyl methyl ketone (54.1 g, 0.75 moles) to obtain an oily layer at the end of the heating period. The oil layer was extracted into chloroform (350 mL), washed with water and dried with anhydrous potassium carbonate. Solvent evaporation yielded the product as a thick oil that turned into a sticky dirty-white solid. This solid was washed quickly with cold water and suction dried to give a white powder (23 g, yield: 41%) that melted at 72° C. IR: 3320, 3128, 2966, 1533, 1457, 1371 cm$^{-1}$; $^1$H NMR (CDCl$_3$, 500 MHz): δ 1.85-1.65 (m, 4H), 1.44-1.36 (4s, 6H), 0.99-0.91 (m, 6H) ppm; $^{13}$C NMR (CDCl$_3$, 125 MHz): δ 207.15, 207.07, 81.24, 81.17, 73.69, 73.51, 35.49, 34.99, 33.85, 33.56, 28,56, 28.29, 27.82, 27.24, 8.55, 8.46, 8.25 ppm.

The product was mixed with neo-DECANOIC ACID PRIME at a 1:1 molar ratio and heated in a sand bath at about 140° C. for one hour and cooled to room temperature.

Example 9

TAIT Mixture Prepared from Acetone/Methyl Isobutyl Ketone/Methyl Ethyl Ketone/Cyclohexanone/Benzaldehyde Combined with neo-DECANOIC ACID PRIME A TAIT mixture was prepared from an equimolar mixture of the five title carbonyl compounds according to the procedure used for preparation of TMIT, using ammonium sulfide (136 mL, 0.4 moles, 20 wt % aqueous solution), sodium cyanide (14.7 g, 0.3 moles), ammonium chloride (16.1 g, 0.3 moles), water (80 mL), cyclohexanone (11.8 g, 0.12 moles), acetone (6.9 g, 0.12 moles) ethyl methyl ketone (8.7 g, 0.12 moles), methyl isobutyl ketone (12.0 g, 0.12 moles), and benzaldehyde (12.7 g, 0.12 moles) to obtain an oily layer at the end of the heating period. The oil layer was extracted into chloroform (350 mL), washed with water and dried with anhydrous potassium carbonate. Solvent evaporation yielded the product as a thick and dark gum (41.5 g, yield: 63% for an average molecular weight of 222). IR: 3140, 2935, 2858, 1656, 1520, 1452, 1376 cm$^{-1}$; $^1$H NMR (CDCl$_3$, 500 MHz): δ7.35-7.15 (m, aromatic), 5.56 (m, benzylic H), 4.97 (m, benzylic H), 2.25-0.8 (several multiplets) ppm; $^{13}$C NMR (CDCl$_3$, 125 MHz): δ 210.4, 210.1, 209.59, 209.54, 208.88, 207.4, 207.2, 206.98, 206.8, 206.50, 206.19, 201.82, 206.72 (and several other peaks in the aliphatic region) ppm. The average molecular weight of 222 was calculated by averaging the molecular weights of the acetone/cyclohexanone cross-product (198) and the cyclohexanone/benzaldehyde cross-product (246), these being the two predominant products among the 8–10 products detected by proton NMR.

The product was mixed with neo-DECANOIC ACID PRIME at a 1:1 molar ratio, based on the average molecular weight determined above, and heated in a sand bath at about 140° C. for one hour and cooled to room temperature.

Example 10

TAIT Mixture Prepared from Acetone/Methyl Isobutyl Ketone/Methyl Ethyl Ketone/Cyclohexanone Combined with neo-DECANOIC ACID PRIME The TAIT mixture described in Example 6 was mixed with neo-DECANOIC ACID PRIME at approximately a 1:1 molar ratio, based on the average molecular weight determined therein, and heated in a sand bath at about 140° C. for one hour and cooled to room temperature.

Example 11

TAIT Mixture Prepared from Methyl Ethyl Ketone Combined with Hydrocinnamic Acid The TAIT mixture described in Example 8 was mixed with hydrocinnamic acid at a 1:1 molar ratio and heated in a sand bath at about 140° C. for one hour and cooled to room temperature.

Example 12

TAIT Mixture Prepared from Methyl Ethyl Ketone Combined with Phenylacetic Acid The TAIT mixture described in Example 8 was mixed with phenylacetic acid at a 1:1 molar ratio and heated in a sand bath at about 140° C. for one hour and cooled to room temperature.

Example 13

TAIT Mixture Prepared from Methyl Ethyl Ketone Combined with Benzoic Acid

The TAIT mixture described in Example 8 was mixed with benzoic acid at a 1:1 molar ratio and heated in a sand bath at about 140° C. for one hour and cooled to room temperature.

Solubility data for the compositions prepared in the Examples in two different lubricating base oils are presented in Tables 1 and 2 by Example number (Ex. No.). The oils used were 105 Coastal Pale FN 1502 oil (CP, available from Exxon Corp.) and Excel 100 HC (EHC, available from Pennzoil Corp.). Also tabulated are the concentration of the composition in the oil as a weight percent (Conc.), the temperature in ° C. to which the composition and oil were heated (T), whether the composition was soluble (Sol.) in the oil and the time after mixing at which haze or solid appeared, given in hours or as an overnight period ("o.n."). Times preceded by a "greater than" symbol (>) indicate that, at the listed time, no more than traces of solid or haze were observed, and that observation of the sample was not continued thereafter.

TABLE 1

| Ex. No. | Oil | Conc. | T | Sol. | time | Notes |
| --- | --- | --- | --- | --- | --- | --- |
| 1 | CP | 3 | 80 | Y | 1 hour | 5–10 min. to dissolve solid |
| 1 | CP | 2 | 80 | Y | o.n. | 5–10 min. to dissolve solid |
| 1 | CP | 1 | 80 | Y | o.n. | 5–10 min. to dissolve solid |
| 2 | CP | 3 | 80 | N | — | |
| 2 | CP | 2 | 80 | N | — | |
| 2 | CP | 1 | 80 | N | — | |
| 3 | CP | 10 | 120 | Y | 1 hour | |
| 3 | CP | 5 | 120 | Y | 4–5 hours | |
| 3 | CP | 2.5 | 120 | Y | 24 hours | |
| 3 | CP | 1 | 120 | Y | 3 days | |
| 3 | EHC | 10 | 160–180 | Y | 10 min. | haze after 3–5 min. at r.t. |
| 3 | EHC | 5 | 160–180 | Y | 15 min. | haze after 5–7 min. at r.t. |
| 3 | EHC | 2.5 | 160–180 | Y | 1 hour | haze after 15 min. at r.t. |

TABLE 1-continued

| Ex. No. | Oil | Conc. | T | Sol. | time | Notes |
|---|---|---|---|---|---|---|
| 3 | EHC | 1 | 160–180 | Y | 4 hours | haze after 1 hour at r.t. |
| 4 | CP | 5 | 140 | N | — | partly insoluble after heating for 20 min. |
| 4 | CP | 2.5 | 140 | Y | 1 hour | |
| 4 | CP | 1 | 140 | Y | 5 hours | |
| 4 | EHC | 10 | 160–180 | N | — | only ca. 50% soluble after heating 20 min. |
| 4 | EHC | 5 | 160–180 | N | — | ca. 10% solid not dissolved after heating 20 min. |
| 4 | EHC | 2.5 | 160–180 | Y | 10 min. | |
| 4 | EHC | 1 | 160–180 | Y | 1 hour | |
| 5 | CP | 20 | 140–160 | Y | 4 days | only 40% precipitated |
| 5 | CP | 10 | 140–160 | Y | >3 weeks | no haze |
| 5 | EHC | 20 | 140–160 | Y | 2 days | ca. 50% precipitated |
| 5 | EHC | 10 | 140–160 | Y | 4 days | ca. 20% precipitated |
| 6 | CP | 20 | 100–120 | Y | >3 weeks | no haze |
| 6 | CP | 10 | 100–120 | Y | >3 weeks | no haze |
| 6 | EHC | 20 | 120–140 | Y | 2 weeks | small amount precipitated |
| 6 | EHC | 10 | 120–140 | Y | >2 weeks | small amount precipitated |

TABLE 2

| Ex. No. | Oil | Conc. | T | Sol. | time | Notes |
|---|---|---|---|---|---|---|
| 7 | EHC | 10 | 140–160 | Y | 5 min. | |
| 7 | EHC | 5 | 140–160 | Y | 30 min. | |
| 7 | EHC | 1 | 140–160 | Y | 1 hour | |
| 8 | EHC | 10 | 140–160 | Y | 8 days | hazy, no solid |
| 8 | EHC | 5 | 140–160 | Y | 8 days | hazy, no solid |
| 8 | EHC | 1 | 140–160 | Y | >8 days | |
| 9 | EHC | 10 | 140–160 | N | — | |
| 9 | EHC | 5 | 140–160 | Y | 4 days | hazy, no solid |
| 9 | EHC | 1 | 140–160 | Y | >4 days | |
| 10 | EHC | 10 | 140–160 | Y | 3 days | hazy, no solid |
| 10 | EHC | 5 | 140–160 | Y | 3 days | hazy, no solid |
| 10 | EHC | 1 | 140–160 | Y | >4 days | |
| 11 | EHC | 10 | 145 | Y | 1 day | some solid |
| 11 | EHC | 5 | 145 | Y | 1 day | hazy, no solid |
| 11 | EHC | 1 | 145 | Y | 5 days | |
| 12 | EHC | 10 | 145 | N | — | hazy solution formed |
| 12 | EHC | 5 | 145 | Y | 1 day | some solid |
| 12 | EHC | 1 | 145 | Y | >7 days | hazy, no solid |
| 13 | EHC | 10 | 145 | Y | 30 min. | |
| 13 | EHC | 5 | 145 | Y | 1 day | some solid |
| 13 | EHC | 1 | 145 | Y | >2 weeks | |

What is claimed is:

1. An oil-soluble lubricant additive composition comprising:

(a) at least one compound of formula

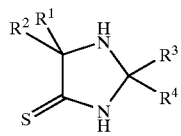

wherein $R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring; and (b) an acid having the formula $RCO_2H$, wherein R is $C_1$–$C_{25}$ alkyl, $C_2$–$C_{25}$ alkenyl, $C_2$–$C_{25}$ alkynyl, $C_5$–$C_{25}$ aryl or $C_5$–$C_{25}$ aralkyl.

2. The oil-soluble lubricant additive composition of claim 1 in which R is $C_5$–$C_{17}$ alkyl, $C_5$–$C_{17}$ alkenyl, $C_5$–$C_{17}$ aryl or $C_5$–$C_{17}$ aralkyl, and a molar ratio of component (a) to component (b) is from 3:1 to 1:5.

3. The oil-soluble lubricant additive composition of claim 2 in which none of $R^1$, $R^2$, $R^3$ or $R^4$ is hydrogen.

4. A composition comprising:

(a) at least one compound of formula

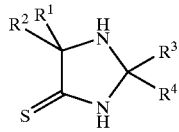

wherein $R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring;

(b) an acid having the formula $RCO_2H$, wherein R is $C_1$–$C_{25}$ alkyl, $C_2$–$C_{25}$ alkenyl, $C_2$–$C_{25}$ alkynyl, $C_5$–$C_{25}$ aryl or $C_5$–$C_{25}$ aralkyl; and (c) a lubricating oil;

wherein components (a) and (b) are present in a total amount from 0.1% to 20% based on total weight of the composition.

5. The composition of claim 4 in which R is $C_5$–$C_{17}$ alkyl, $C_5$–$C_{17}$ alkenyl, $C_5$–$C_{17}$ aryl or $C_5$–$C_{17}$ aralkyl, and a molar ratio of component (a) to component (b) is from 3:1 to 1:5.

6. The composition of claim 5 in which none of $R^1$, $R^2$, $R^3$ or $R^4$ is hydrogen.

7. The composition of claim 6 in which components (a) and (b) are present in a total amount from 0.5% to 3% based on total weight of the composition.

8. A composition produced by blending:

(a) at least one compound of formula

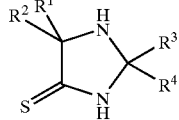

wherein $R^1$, $R^2$, $R^3$ and $R^4$ are independently hydrogen, alkyl, alkenyl, aryl or aralkyl; or $R^1$ and $R^2$, or $R^3$ and $R^4$, combine with the carbon atom to which they are attached to form an alkyl or alkenyl ring;

(b) an acid having the formula $RCO_2H$, wherein R is $C_1$–$C_{25}$ alkyl, $C_2$–$C_{25}$ alkenyl, $C_2$–$C_{25}$ alkynyl, $C_5$–$C_{25}$ aryl or $C_5$–$C_{25}$ aralkyl; and (c) a lubricating oil;

wherein components (a) and (b) are added in a total amount from 0.1% to 20% based on total weight of the composition.

9. The composition of claim 8 in which R is $C_5$–$C_{17}$ alkyl, $C_5$–$C_{17}$ alkenyl, $C_5$–$C_{17}$ aryl or $C_5$–$C_{17}$ aralkyl, and component (a) and component (b) are added in a molar ratio from 3:1 to 1:5.

10. The composition of claim 9 in which none of $R^1$, $R^2$, $R^3$ or $R^4$ is hydrogen, and components (a) and (b) are added in a total amount from 0.5% to 3% based on total weight of the composition.

* * * * *